US009457110B2

(12) United States Patent
Vogt

(10) Patent No.: US 9,457,110 B2
(45) Date of Patent: Oct. 4, 2016

(54) METHOD AND COMPOSITION FOR STERILIZATION OF A POLYMERIZABLE MONOMER

(71) Applicant: HERAEUS MEDICAL GMBH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 698 days.

(21) Appl. No.: 13/681,996

(22) Filed: Nov. 20, 2012

(65) Prior Publication Data
US 2013/0125786 A1    May 23, 2013

Related U.S. Application Data

(60) Provisional application No. 61/562,701, filed on Nov. 22, 2011.

(30) Foreign Application Priority Data

Nov. 22, 2011  (EP) .................................. 11 009 254

(51) Int. Cl.
A61L 2/18 (2006.01)
A61L 24/04 (2006.01)
A61L 2/16 (2006.01)

(52) U.S. Cl.
CPC .. *A61L 2/18* (2013.01); *A61L 2/16* (2013.01); *A61L 24/046* (2013.01); *A61L 2430/02* (2013.01)

(58) Field of Classification Search
CPC ......... A61L 2/18; A61L 2/16; A61L 24/046; A61L 2430/02
USPC .......................... 106/287.2; 422/28; 523/116
See application file for complete search history.

(56) References Cited

U.S. PATENT DOCUMENTS

| | | | | |
|---|---|---|---|---|
| 3,997,400 | A * | 12/1976 | Heden ............................ | 435/161 |
| 4,946,648 | A | 8/1990 | Dichtelmuller et al. | |
| 6,197,573 | B1 * | 3/2001 | Suryanarayan et al. ... | 435/286.7 |
| 6,458,868 | B1 * | 10/2002 | Okada et al. ................ | 523/116 |
| 6,664,095 | B1 | 12/2003 | Suryanarayan et al. | |
| 7,714,097 | B2 | 5/2010 | Zhang et al. | |
| 2003/0211131 | A1 | 11/2003 | Martin et al. | |
| 2004/0149634 | A1* | 8/2004 | Hughes ........................ | 210/96.1 |
| 2006/0247328 | A1* | 11/2006 | Nakata et al. ................ | 523/109 |
| 2006/0263329 | A1 | 11/2006 | Eemeta et al. | |
| 2007/0082935 | A1 | 4/2007 | Chia et al. | |
| 2007/0202177 | A1 | 8/2007 | Hoang | |
| 2009/0105366 | A1 | 4/2009 | Vogt et al. | |
| 2010/0035997 | A1 | 2/2010 | Broadley et al. | |
| 2010/0159027 | A1 | 6/2010 | Vogt et al. | |
| 2011/0034622 | A1* | 2/2011 | Kawamura et al. .......... | 524/548 |

FOREIGN PATENT DOCUMENTS

| | | |
|---|---|---|
| CN | 1943793 A | 4/2007 |
| DE | 3900862 A1 | 7/1990 |
| DE | 102007019044 A1 | 10/2008 |
| DE | 102008030312 A1 | 1/2010 |
| EP | 0364842 A1 | 4/1990 |
| EP | 2052748 A2 | 4/2009 |
| EP | 2198893 A2 | 6/2010 |
| JP | 57-042650 A | 3/1982 |
| JP | 57-062229 A | 4/1982 |
| JP | H01-100129 A | 4/1989 |
| JP | H07-267997 A | 10/1995 |
| JP | 2003-529316 A | 10/2003 |
| JP | 2004-188679 A | 7/2004 |
| JP | 2009-528360 A | 8/2009 |
| JP | 2010-144168 A | 7/2010 |
| KR | 2008-0052865 A | 6/2008 |
| WO | 2005021470 A2 | 3/2005 |
| WO | 2007117499 A2 | 10/2007 |

OTHER PUBLICATIONS

Charnley, "Anchorage of the Femoral Head Prosthesis to the Shaft of the Femur", The Journal of Bone and Joint Surgery, vol. 42 B, No. 1, pp. 28-30 (1960).
Office Action issued May 31, 2013 in AU Application No. 2012254902.
Office Action issued Sep. 16, 2014 in CN Application No. 201210477342.3.
English translation of an Office Action issued Apr. 1, 2014 in JP Application No. 2012-248143.
Gould, "Mechanisms of Resistance and Dormancy," Chapter 5 of The Bacterial Spore, vol. 2, Academic Press, Inc., London, pp. 173-209 (1984).
Borick, "Chemical Sterilizers (Chemosterilizers)," Adv. Appl. Microbiol., vol. 10, pp. 291-312 (1968).
Search Report issued May 4, 2012 in EP Application No. 11009254.1.
Kuzmenko et al, "Use of beta propiolactone for sterilization of bone tissue. Experimental study", Ortortravm-Prcjtez, vol. 30, No. 2, pp. 59-63 (1969) (abstract only).

(Continued)

*Primary Examiner* — Alexander Polyansky
(74) *Attorney, Agent, or Firm* — Panitch Schwarze Belisario & Nadel LLP

(57) ABSTRACT

A method is provided for sterilization of a polymerizable monomer, in which the mixture contains at least the polymerizable monomer, a compound (a), and a compound (b). Compound (a) is selected from the group of compounds (a1), compounds (a2), and compounds (a3), wherein compounds (a1) are represented by general formula (I):

(I)

$$\begin{array}{c} O \\ \parallel \\ R_4 - \overset{|}{\underset{R_3}{C}} - \overset{|}{\underset{R_2}{C}} - R_1 \\ \end{array}$$

wherein R1, R2, R3, and R4, independent of each other, represent a substituted alkyl residue, a non-substituted alkyl residue, a halogen, a nitro group, or a cyano group; compounds (a2) are selected from the group of dimers of compounds (a1); and compounds (a3) are selected from the group of dialkyldicarbonates. Compound (b) is selected from the group of water and alcohols.

6 Claims, No Drawings

(56) References Cited

OTHER PUBLICATIONS

Sutherland et al, "Graft sterilization. A Bacteriological and histological study of the relative merits of ethylene oxide and [beta]-propiolactone as tissue sterilizing agents, with special reference to arterial grafts", British Medical Journal, vol. 5073, pp. 734-736 (1958) (abstract only).

* cited by examiner

METHOD AND COMPOSITION FOR STERILIZATION OF A POLYMERIZABLE MONOMER

CROSS-REFERENCE TO RELATED APPLICATIONS

The present application claims the benefit of U.S. Provisional Patent Application No. 61/562,701, filed Nov. 22, 2011, the subject matter of which is hereby incorporated by reference.

BACKGROUND OF THE INVENTION

The invention relates to a method for sterilization of a polymerizable monomer, in particular to sterilization of a monomer for radical polymerization. The invention also relates to mixtures containing a polymerizable monomer, in particular a monomer for radical polymerization, a kit for producing bone cement containing one of these mixtures, and a bone cement paste containing one of these mixtures.

Conventional poly(methylmethacrylate) bone cements (PMMA bone cements) have been known for decades and are based on the ground-breaking work of Sir Charnley (Charnley, J.: "Anchorage of the Femoral Head Prosthesis of the Shaft of the Femur." *J. Bone Joint Surg.* 42: 28-30 (1960)).

The basic structure of PMMA bone cements has remained the same ever since. PMMA bone cements consist of a liquid monomer component and a powder component. The monomer component generally contains (i) the monomer, methylmethacrylate, and (ii) an activator (e.g. N,N-dimethyl-p-toluidine) dissolved therein. The powder component comprises (i) one or more polymers that are made by polymerization, preferably suspension polymerization, based on methylmethacrylate and co-monomers, such as styrene, methylacrylate or similar monomers, (ii) a radioopaquer, and (iii) an initiator, (e.g. dibenzoylperoxide). Mixing the powder component and the monomer component, the polymers of the powder component in the methylmethacrylate swell which generates a dough that can be shaped plastically. Simultaneously, the activator, N,N-dimethyl-p-toluidine, reacts with dibenzoylperoxide which disintegrates and forms radicals in the process. The radicals formed trigger the radical polymerization of the methylmethacrylate. Upon advancing polymerization of the methylmethacrylate, the viscosity of the cement dough increases until the cement dough solidifies and thus is cured.

German Patent DE 10 2007 050 762 B3 proposes a kit for producing bone cement comprising two pastes as an alternative to the conventional powder-liquid polymethylmethacrylate bone cements. These pastes each contain a polymerizable monomer, such as, for example, a methacrylate monomer for radical polymerization, a polymer soluble in the methacrylate monomer, and a particulate polymer insoluble in the methacrylate monomer. In addition, one of these pastes contains a radical polymerization initiator, whereas the other paste comprises a polymerization activator. As a result of the selected composition, the bone cement produced from these pastes possesses sufficiently high viscosity and cohesion in order to withstand the pressure from bleeding until it is fully cured. When the two pastes are mixed, the polymerization initiator reacts with the accelerator to form radicals that initiate the radical polymerization of the methacrylate monomers. Owing to the advancing polymerization, the paste is cured while the methacrylate monomers are consumed. The pastes contained in the kit for producing bone cement are non-aqueous systems. Accordingly, the pastes contain at most only traces of water.

PMMA bone cements are medical products of class IIb, or medical products of class III if antibiotics are added. In order to ensure the safety of the patients, the PMMA bone cements may be marketed in sterile condition in a doubly-sterile package only. In conventional PMMA bone cements consisting of a liquid monomer component and a powder component, the powder component is sterilized by subjecting it to ethylene oxide. Sterilization of the powder component by gamma irradiation is customary as well.

Often used for producing the monomer component, the polymerizable monomer, methylmethacrylate, is biocidal for most vegetative microbial life forms due to its lipophilic and thus denaturing properties. Therefore, these micro-organisms cannot exist in anhydrous methylmethacrylate. However, aside from the vegetative forms, micro-organisms also have generative forms, such as endospores. These generative survival forms of micro-organisms are formed by gram-positive bacteria, in particular of the *Bacillus* and *Clostridium* genus, as a means of persisting during unfavorable living conditions. In their resting state, endospores have no active metabolism and possess a multi-layered spore capsule that largely protects the core of the spore from the action of chemicals and other environmental effects. This renders spores extremely resistant to the action of heat and chemicals (Borick, P. M.: "Chemical Sterilizers," *Adv. Appl. Microbiol.* 10: 291-312 (1968); Gould, G. W.: "Recent Advances in the Understanding of Resistance and Dormancy in Bacterial Spores," *J. Appl. Bacteriol.* 42: 297-309 (1977); Gould, G. W.: "Mechanisms of Resistance and Dormancy," in Hurst, A. and Gould, G. W. (ed.), *The Bacterial Spore*, Academic Press, Inc. New York, 2:173-209 (1983)). Due to their high resistance, endospores are used as bio-indicators for validation and control of the efficacy of sterilization processes. This is based on the assumption that the inactivation of endospores is indicative of all vegetative microbial forms of life being killed. Endospores of gram-positive bacteria are classified in international resistance class III. Resistance class I includes non-spore-forming bacteria and vegetative forms of spore-forming bacteria and resistance class II includes spores that are killed within a few minutes in a flow of steam at 105° C. In accordance with DAB 2008 (*Deutsches Arzneimittelbuch*—German Medicine Book), all micro-organisms of resistance classes I-III must be killed or inactivated irreversibly.

Accordingly, there is a fundamental need to have methods for efficient sterilization of polymerizable monomers, in particular of monomers for radical polymerization.

Methods for sterilization of polymerizable monomers are known in the field of medical products. It is common to use physical sterilization methods for sterilization of medical products. In particular gamma irradiation, electron bombardment, UV irradiation, heat sterilization, and autoclaving with pressurized steam need to be mentioned in this context. However, these sterilization methods are inherently disadvantageous due to the extensive use of equipment and process resources required by them. Sterilization of polymerizable monomers by means of these physical sterilization methods is inapplicable for other reasons as well though. For example, subjecting the materials to heat, gamma irradiation or X-ray irradiation would initiate radical polymerization of the polymerizable monomers which would result in inadvertent premature curing of the bone cement. Steam sterilization, in contrast, would result in hydrolysis of the polymerizable monomers which would prevent polymerization of the polymerizable monomers.

Sterilization of polymerizable monomers is often attained through sterile filtration and subsequent aseptic packing. However, the aseptic production of polymerizable monomers is very expensive. Another associated problem is that viruses cannot be removed through sterile filtration. Moreover, sterilization of pastes for producing bone cement by means of sterile filtration is not feasible due to the high viscosity of the pastes and the radio-opaquers and filling agents contained in the pastes.

Aside from these physical methods, it is customary to use chemical compounds for sterilization of medical products. These include, for example, ethylene oxide, formaldehyde, glutardialdehyde, o-phthaldialdehyde, hypochlorite, chlorine dioxide, peracetic acid, and hydrogen peroxide. However, the use of these compounds is associated with significant disadvantages. For example ethylene oxide is sporocidal only in the presence of moisture such that its use in the absence of water does not result in the desired sterilization effect. Moreover, pastes for producing bone cement are usually available in closed diffusion-tight film pouches or closed plastic cartridges. Ethylene oxide is incapable of penetrating into these containers, however the packaged pastes cannot be sterilized by this method. In contrast, aldehydes are usually applied as aqueous solutions or in the gaseous state in the case of formaldehyde due to their mechanism of action. Peracetic acid and hydrogen peroxide are strong oxidizing agents which are also used in the form of aqueous solutions. However, for this reason, these compounds are not suitable for sterilization of mixtures that must contain only small amounts of water, if any. Chlorine-based compounds are usually very effective sterilization agents. They are disadvantageous though in that chlorine-containing secondary products remain in the medical product after sterilization.

It is known from pharmaceutical industry that aqueous protein solutions, such as, e.g., vaccines, are very sensitive to the effects of oxidizing sterilization agents and various physical sterilization methods, for example sterilization with gamma radiation. For this reason, aqueous protein solutions often have small amounts of the acylating agent, β-propiolactone, added to them for the purpose of sterilization. β-propiolactone can be used inactivate both viruses and spores, in particular endospores. These effects are likely to occur due to acylation of the amino groups of DNA/RNA or proteins. The water present as solvent is capable of slowly decomposing zβ-propiolactone such that no active β-propiolactone is present any longer in aqueous protein solutions after just a short period of time. The principle of sterilization of aqueous protein solutions by means of acylating agents, such as β-propiolactone, is based on the fact that spores can swell in small amounts of aqueous media. This swelling renders the double walls of spores permeable to acylating agents, such that the acylating agents can penetrate into the spores and be effective therein.

However, swelling of the spores is not feasible in mixtures containing a polymerizable monomer and only small quantities of water, if any. Therefore, swelling cannot be used in preparation of the penetration of the acylating agent into spores. Accordingly, sterilization of these mixtures by means of acylating agents, such as β-propiolactone, appears not to be feasible.

BRIEF SUMMARY OF THE INVENTION

The invention is therefore based on providing an effective method for sterilization of a polymerizable monomer, in particular a monomer for radical polymerization. The method is to produce, in particular, mixtures that are free of endospores. Preferably, the method should be suitable for sterilization of polymerizable monomers, in particular of monomers for radical polymerization, in mixtures containing no or only small quantities of water, for example no more than 2.0% by weight of water, more preferably no more than 1.0% by weight of water, and even more preferably no more than 0.5% by weight of water, relative to the total weight of the mixture. Moreover, it is preferable for the mixture to contain no toxic or harmful residues, such as, for example, chlorine-containing residues, after the sterilization is completed. Moreover, it is preferable to also overcome other disadvantages known from the prior art.

Further objects underlying the invention include the provision of a mixture (I) that can be used for sterilization according to the method according to the invention, a mixture (II) that can be obtained while carrying out the method according to the invention, a kit for producing bone cement that can be obtained after carrying out the method according to the invention, and a bone cement paste that can be obtained after carrying out the method according to the invention.

Accordingly, the invention provides a method for sterilization of a polymerizable monomer, in particular of a monomer for radical polymerization, in which a mixture (I) is produced, the mixture (I) comprising at least the polymerizable monomer, in particular the monomer for radical polymerization, a compound (a) and a compound (b), wherein:
  (i) compound (a) is selected from compounds (a1) selected from the group consisting of compounds represented by formula (I):

wherein R1, R2, R3, and R4 independently represent a hydrogen, a substituted alkyl residue, a non-substituted alkyl residue, a halogen, a nitro group, or a cyano group; compounds (a2) selected from the group consisting of dimers of compounds (a1); and compounds (a3) selected from the group consisting of dialkyldicarbonates; and
  (ii) compound (b) is selected from the group consisting of water and alcohols;
wherein the fraction of compound (b) in mixture (I) is preferably no more than 2% by weight, relative to the total weight of the mixture (I).

The invention also provides a mixture (I), the mixture (I) comprising at least one polymerizable monomer, in particular a monomer for radical polymerization, a compound (a) and a compound (b), wherein:
  (i) compound (a) is selected from compounds (a1) selected from the group consisting of compounds represented by formula (I):

wherein R1, R2, R3, and R4 independently represent a hydrogen, a substituted alkyl residue, a non-substituted alkyl residue, a halogen, a nitro group, or a cyano group; compounds (a2) selected from the group consisting of dimers of compounds (a1); and compounds (a3) selected from the group consisting of dialkyldicarbonates; and (ii) compound (b) is selected from the group consisting of water and alcohols;

wherein the fraction of compound (b) in mixture (I) is no more than 2% by weight, relative to the total weight of mixture (I).

The invention further provides a mixture (II), the mixture comprising at least one polymerizable monomer, in particular a monomer for radical polymerization, and a compound (c), wherein compound (c) is selected from the group consisting of alcohols, carboxylic acids having at least three carbon atoms, and esters, and can be obtained by reacting a compound (a) and a compound (b), wherein:

(i) compound (a) is selected from compounds (a1) selected from the group consisting of compounds represented by formula (I):

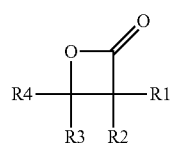

(I)

wherein R1, R2, R3, and R4 independently represent a hydrogen, a substituted alkyl residue, a non-substituted alkyl residue, a halogen, a nitro group, or a cyano group; compounds (a2) selected from the group consisting of dimers of compounds (a1); and compounds (a3) selected from the group consisting of dialkyldicarbonates; and (ii) compound (b) is selected from the group consisting of water and alcohols.

Moreover, the invention provides a kit for producing bone cement comprising at least one paste A and one paste B, wherein at least one of paste A and paste B contains a mixture (II) according to the description provided herein.

Moreover, the invention provides a bone cement paste containing a mixture (II) according to the description provided herein.

The invention is partly based on the surprising finding that sterilization of a polymerizable monomer, in particular of a monomer for radical polymerization, by an acylating agent according to compound (a) in mixtures is feasible even if the fraction of water in these mixtures is no more than 2% by weight, more preferably no more than 1.0% by weight, and even more preferably no more than 0.5% by weight, relative to the total weight of the mixture. Although the spores contained in the mixture cannot swell at this low quantity of water, the polymerizable monomer in the mixture is sterilized effectively, which was surprising.

Moreover, another surprising finding is that neither compound (a) nor the products obtained by reacting compound (a) and compound (b) inhibit the polymerization of the polymerizable monomers. This is true also when further components are contained in the mixture being subjected to the method for sterilization, such as, for example, components of a paste for producing bone cement.

DETAILED DESCRIPTION OF THE INVENTION

The invention relates to a method for sterilization of a polymerizable monomer, in particular of a monomer for radical polymerization.

A polymerizable monomer characterized by sterility is obtained in the method according to the invention. In the scope of the invention, "sterility" shall be understood to mean a state that is free of viable micro-organisms. In this context, please refer to the corresponding definition provided in EN 556-1:2001.

At least one polymerizable monomer, in particular at least one monomer for radical polymerization, is being subjected to the method for sterilization.

Polymerizable monomer shall be understood to preferably mean compounds that comprise at least one polymerizable olefinic bond. In a broader scope, the term, polymerizable monomer, shall also be understood to mean macromers having terminal methacrylate groups, acrylate groups, itaconate groups, maleinate groups or fumarate groups. These macromers can be liquid or semi-liquid. Moreover, these macromers can be linear or branched compounds.

The polymerizable monomer, in particular the monomer for radical polymerization, used according to the invention preferably has a molar mass of less than 1,000 g/mol. This also comprises polymerizable monomers that are components of a mixture of monomers, wherein at least one of the polymerizable monomers of the mixture of monomers has a defined structure with a molar mass of less than 1,000 g/mol.

According to a preferred embodiment, the polymerizable monomer is selected from the group consisting of methacrylic acid esters (preferably mono-functional and multi-functional methacrylic acid esters), acrylic acid esters (preferably mono-functional and multi-functional acrylic acid esters), methacrylamide, methacrylic acid, acrylic acid, itaconic acid esters, itaconic acid, maleic acid esters, maleic acid, fumaric acid esters, and fumaric acid. The methacrylic acid esters and acrylic acid esters preferably are alkyl esters of methacrylic acid and acrylic acid, respectively. In this context, the alkyl group of the alkyl esters preferably has a chain length of 1-10 carbon atoms, more preferably a chain length of 1-4 carbon atoms, even more preferably a chain length of 1-2 carbon atoms, and most preferably one carbon atom. According to a particularly preferred embodiment, the polymerizable monomer is selected from the group consisting of methacrylic acid methylester, methacrylamide, and ethylene glycol dimethacrylate.

A mixture (I) is produced for sterilization of the polymerizable monomer. Mixture (I) preferably is self-sterilizing. A mixture is preferably said to be self-sterilizing if sterilization does not necessitate the addition of any further components or the influence of external factors, such as irradiation.

Mixture (I) contains at least one compound (a) aside from the polymerizable monomer. Preferably, compound (a) is an acylating agent. Preferably, the acylating agent is capable of acylating amino groups of DNA/RNA or proteins. Compound (a) is therefore capable of killing micro-organisms and thus has a sterilizing effect.

Compound (a) is selected from the group consisting of compounds (a1), (a2), and (a3) according to the description provided herein.

Compound (a) can be a compound (a1) represented by the general formula (I):

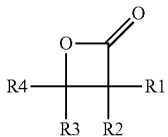

In formula (I), R1, R2, R3, and R4 independently represent hydrogen, a substituted alkyl residue, a non-substituted alkyl residue, halogen, a nitro group, or a cyano group.

The stereochemistry of compounds (a1) is not limited in any way. Preferably, the scope of the invention includes all isomers of compounds (a1) represented by general formula (I), regardless of their exact configuration.

The alkyl residues can be substituted or non-substituted alkyl residues, independent of each other. At least one substituent of a substituted alkyl residue is preferably selected from the group consisting of halogen residues, nitro residues, and cyano residues.

The alkyl residues can be saturated or unsaturated alkyl residues, independent of each other. Preferably, an unsaturated alkyl residue comprises at least one carbon-carbon double bond.

The alkyl residues can be branched or unbranched alkyl residues, independent of each other. It is preferable for alkyl residues R1, R2, R3, and R4 to be unbranched alkyl residues.

Independent of each other, the alkyl residues have a main chain length in the range of 1-4 carbon atoms, more preferably a main chain length in the range of 1-2 carbon atoms, and even more preferably one carbon atom.

Fluorine residues, chlorine residues, and bromine residues are preferred halogen residues in general formula (I). Residues R1, R2, R3, and R4, can represent one or more halogen residues, independent of each other.

According to a preferred embodiment, residues R1, R2, R3, and R4 each represent hydrogen.

According to another preferred embodiment, residue R1 represents a methyl residue and residues R2, R3, and R4 represent hydrogen.

According to another preferred embodiment, residues R1, R2, and R3 represent hydrogen and residue R4 represents a methyl residue.

According to yet another preferred embodiment, residues R1 and R3 represent hydrogen and residues R2 and R4 represent a methyl residue.

According to a particularly preferred embodiment, compound (a1) is β-propiolactone (CAS number 57-57-8).

Compound (a) can also be a compound (a2), wherein compound (a2) is a dimer of any of compounds (a1). A dimer of compound (a1) is preferably represented by general formula (II):

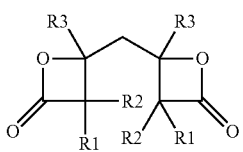

wherein residues R1, R2, and R3, independent of each other, can have the meanings defined above.

The stereochemistry of compounds (a2) is not limited in any way. Preferably, the scope of the invention includes the use, as compound (a2), of all dimers of compound (a1), in particular of all isomers represented through general formula (II), regardless of their exact configuration.

According to a particularly preferred embodiment, residues R1, R2, and R3 in formula (II) each represent hydrogen.

Compound (a) can also be a compound (a3) selected from the group consisting of dialkyldicarbonates.

Dialkyldicarbonates can be represented by the following general formula (III):

R5-O—CO—O—CO—O—R6      (III).

Residues R5 and R6 can be different from each other or identical. Preferably, residues R5 and R6 are identical.

Residues R5 and R6 can be saturated residues or unsaturated residues, independent of each other. In this context, unsaturated residues comprise at least one carbon-carbon double bond.

Residues R5 and R6 can be branched alkyl residues or unbranched alkyl residues, independent of each other. Preferably, residues R5 and R6 are unbranched.

Residues R5 and R6 can be substituted alkyl residues or non-substituted alkyl residues, independent of each other. Halogen substituents, for example, preferably chlorine substituents, are conceivable as substituents of residues R5 and R6. Preferably, residues R5 and R6 are non-substituted.

According to a preferred embodiment, residues R5 and R6, independent of each other can have a main chain length in the range of 1-8 carbon atoms, more preferably a main chain length in the range of 1-4 carbon atoms, even more preferably a main chain length in the range of 1-2 carbon atoms, and particularly preferably a main chain length of one carbon atom.

According to a particularly preferred embodiment, compound (a) is β-propiolactone (CAS number 57-57-8).

Preferably, the fraction of compound (a) in mixture (I) is at least 0.0001% by weight, more preferably at least 0.001% by weight, even more preferably at least 0.01% by weight, and particularly preferably at least 0.1% by weight, relative to the total weight of mixture (I). Preferably, the fraction of compound (a) in mixture (I) is no more than 50% by weight, more preferably no more than 5% by weight, even more preferably no more than 2% by weight, and particularly preferably no more than 0.4% by weight, relative to the overall weight of mixture (I). The fraction of compound (a) in mixture (I) is preferably in the range of 0.0001-50% by weight, more preferably in the range of 0.001-5% by weight, even more preferably in the range of 0.001-2% by weight, and particularly preferably in the range of 0.1-0.4% by weight, relative to the total weight of mixture (I).

Mixture (I), which is being produced for sterilization of the polymerizable monomer, also contains a compound (b).

Compound (b) is preferably selected from the group consisting of water and alcohols. It is preferable for the water to be doubly distilled water. Preferably, the water is pyrogen-free. The structure of the alcohol is not limited in any way.

Preferably, the alcohol has a main chain length of 1-20 carbon atoms, more preferably a main chain length of 1-10 carbon atoms, and even more preferably a main chain length of 1-4 carbon atoms.

The alcohol can be a saturated or an unsaturated alcohol. If the alcohol is unsaturated, the alcohol preferably contains at least one carbon-carbon double bond.

Moreover, the alcohol can be substituted or non-substituted. At least one substituent of the substituted alcohol is preferably selected from the group consisting of halogen substituents, nitro substituents, and cyano substituents.

The alcohol can be a monoalcohol or a polyalcohol. Preferably, the alcohol is a monoalcohol.

The alcohol can be a branched or an unbranched alcohol. Preferably, the alcohol is an unbranched alcohol.

The alcohol is preferably selected from the group consisting of primary and secondary alcohols.

The alcohol shall preferably be represented by the following general formula (IV):

R7-OH  (IV).

The residue R7 is not subject to any limitation. Preferably, the residue R7 is an alkyl residue. Preferably, the alkyl residue has a main chain length of 1-20 carbon atoms, more preferably a main chain length of 1-10 carbon atoms, even more preferably a main chain length of 1-5 carbon atoms, particularly preferably a main chain length of 1-2 carbon atoms, and particularly preferably a main chain length of 1 carbon atom. The alkyl residue can be saturated or unsaturated. The residue R7 can be substituted or non-substituted. Conceivable substituents are, for example, hydroxyl groups, nitro groups, cyano groups, and halogens. The residue R7 can be branched or unbranched.

According to a preferred embodiment, the primary alcohol is selected from the group consisting of methanol, ethanol, ethylene glycol, diethylene glycol, triethylene glycol, tetraethylene glycol, and pentaerythritol. The term primary alcohol shall preferably include polymerizable monomers, in particular monomers for radical polymerization, having alcoholic hydroxyl groups, such as, for example, methacrylic acid-2-hydroxyethylester.

According to another preferred embodiment, the secondary alcohol is selected from the group consisting of isopropanol and butan-2-ol.

According to a particularly preferred embodiment, the alcohol is selected from the group consisting of methanol, ethanol, diethylene glycol, triethylene glycol, and tetraethylene glycol.

The scope of the invention also includes that the polymerizable monomer and compound (b) in mixture (I) may be the same compound. For example methacrylic acid-2-hydroxyethylester can be both the sterilizing polymerizable monomer and also compound (b).

Preferably, the fraction of compound (b) in mixture (I) is at least 0.0001% by weight, more preferably at least 0.001% by weight, even more preferably at least 0.01% by weight, and particularly preferably at least 0.1% by weight, relative to the total weight of mixture (I). Preferably, the fraction of compound (b) in mixture (I) is no more than 2.0% by weight, more preferably no more than 1.0% by weight, even more preferably no more than 0.5% by weight, and particularly preferably no more than 0.4% by weight, relative to the overall weight of mixture (I). The fraction of compound (b) preferably is in the range of 0.0001-2.0% by weight, more preferably in the range of 0.001-1.0% by weight, even more preferably in the range of 0.001-0.5% by weight, and particularly preferably in the range of 0.1-0.4% by weight, relative to the total weight of mixture (I).

According to a preferred embodiment, the ratio of the quantity of compound (b), $n_b$, contained in mixture (I) to the quantity of compound (a), $n_a$, contained in mixture (I) is represented by the in equation $n_b/n_a > 0.5$, more preferably by the in equation $n_b/n_a > 0.8$, and even more preferably by the in equation $n_b/n_a > 1$.

In addition to the polymerizable monomer, compound (a) and compound (b), mixture (I) can optionally contain at least one additional component (d).

The scope of the invention includes, for example, that mixture (I) is a part of a medical product that contains compounds (a) and (b) in addition to the polymerizable monomer, in particular the monomer for radical polymerization. The scope of the invention includes, in particular, carrying out the method for sterilization of a polymerizable monomer in a mixture (I) that contains, aside from compounds (a) and (b), at least one, but preferably all, components that are contained in a kit for producing a bone cement, wherein the component can, for example, be a paste. Accordingly, mixture (I) can also be a mixture containing, aside from compound (a) and compound (b), the components of a polymethylmethacrylate bone cement that are described in German Patents DE 10 2007 052/16, DE 10 2007 050 762 or DE 10 2010 005 956. Moreover, mixture (I) can also be a mixture containing, aside from compounds (a) and (b), the components of inorganic bone cements or of polymerizable dental materials. Mixture (I) can also be a mixture that contains, aside from compound (a) and compound (b), the components of a monomer liquid contained in a kit for producing bone cement (for example polymethylmethacrylate bone cement).

Conceivable as additional components (d) are preferably substances selected from the group consisting of polymers (d1) soluble in the polymerizable monomer, polymers (d2) insoluble in the polymerizable monomer, radical polymerization initiators (d3), polymerization activators (d4), filling agents (d5), colorants (d6), pharmaceutical agents (d7), and mixtures thereof.

According to a preferred embodiment, the additional component (d) is a polymer (d1) soluble in the polymerizable monomer. The polymer (d1) soluble in the polymerizable monomer is preferably a polymer having a mean molar mass (by weight) of less than 500,000 g/mol and is more preferably a polymer having a mean molar mass (by weight) of less than 150,000 g/mol. The specification of the molar mass refers to the molar mass determined by viscometry. The soluble polymer (d1) can be either cross-linked or non-crosslinked, and is preferably non-crosslinked. The soluble polymer (d1) can be a homopolymer or a copolymer. Preferably, the soluble polymer (d1) is a polymer of a methacrylic acid ester.

According to a particularly preferred embodiment, the soluble polymer (d1) is a copolymer of methacrylic acid methylester. According to another particularly preferred embodiment, the soluble polymer (d1) is selected from the group consisting of poly(methacrylic acid methylester) (PMMA), poly(methacrylic acid ethylester) (PMAE), poly(methacrylic acid propylester) (PMAP), poly(methacrylic acid isopropylester), poly(methylmethacrylate-co-methylacrylate), and poly(styrene-co-methylmethacrylate).

The polymer (d1) is soluble in the polymerizable monomer. According to definition, the polymer is soluble in the polymerizable monomer if the solubility of the polymer in the polymerizable monomer at a temperature of 25° C. is at least 25 g/l, more preferably at least 50 g/l, and most preferably at least 100 g/l.

According to another preferred embodiment, the additional component (d) is a polymer (d2) insoluble in the polymerizable monomer. Preferably, the insoluble polymer (d2) is particulate. According to a particularly preferred embodiment, the insoluble polymer (d2) has an average particle size in the range of 100 nm-500 μm. The average particle size shall be understood herein to mean a size range that applies to at least 90 percent of the particles. The insoluble polymer (d2) preferably has a mean molar mass (by weight) of at least 150,000 g/mol and more preferably a mean molar mass (by weight) of at least 500,000 g/mol. The specification of the molar mass refers to the molar mass determined by viscometry. The insoluble polymer (d2) can be either crosslinked or non-crosslinked, and preferably is crosslinked. In this context, the cross-linking is effected through a difunctional compound. The difunctional compound can be selected, for example, from the group consisting of alkylene glycol dimethacrylates. An expedient cross-linker is, for example, ethylene glycol dimethacrylate. The insoluble polymer (d2) can be a homopolymer or a copolymer. Preferably, the insoluble polymer (d2) is a polymer of a methacrylic acid ester. According to a preferred embodiment, the insoluble polymer (d2) is a homopolymer or a copolymer of a methacrylic acid alkylester.

According to a particularly preferred embodiment, the insoluble polymer (d2) is selected from the group consisting of cross-linked poly(methylmethacrylate-co-methacrylate) and cross-linked poly(methylmethacrylate). The insoluble polymer (d2) is insoluble in the polymerizable monomer. According to definition, the polymer is insoluble in the polymerizable monomer, if the solubility of the polymer in the polymerizable monomer at a temperature of 25° C. is less than 50 g/l, is preferably less than 25 g/l, is more preferably less than 10 g/l, and is even more preferably less than 5 g/l.

According to yet another preferred embodiment, the additional component (d) is a radical polymerization initiator (d3).

According to yet another preferred embodiment, the additional component (d) is a polymerization activator (d4). The polymerization activator can be present in addition to or alternatively to the radical polymerization initiator (d3).

According to yet another preferred embodiment, the additional component (d) is a filling agent (d5). Preferably, the filling agent (d5) is selected from the group consisting of inorganic filling agents, organic filling agents, glass, metals, and carbon. Preferably, inorganic filling agents are selected from the group consisting of calcium sulfates (such as calcium sulfate, calcium sulfate dihydrate or calcium sulfate hemihydrate), calcium carbonate, calcium phosphates (such as α-tricalcium phosphate or β-tricalcium phosphate), hydroxylapatite, barium sulfate, and zirconium dioxide. Organic filling agents are preferably selected from the group consisting of non-crosslinked polymer particles, cross-linked polymer particles, and polymer fibers. The glass, as a filling agent, can be present, for example, in the form of a glass powder or in the form of glass fibers. The metal can preferably be tantalum or zirconium.

According to yet another preferred embodiment, the additional component (d) is a colorant (d6).

According to yet another preferred embodiment, the additional component (d) is a pharmaceutical agent (d7). Preferably, the pharmaceutical agent (d7) is selected from the group consisting of antibiotics, anti-infective agents, antiseptic agents, antiphlogistic agents, and growth factors.

The mixture (I) can be liquid or semi-liquid at room temperature and a pressure of 1.013 bar.

According to a preferred embodiment, mixture (I) containing at least the polymerizable monomer, compound (a) and compound (b), is present in a package. Preferably, the package is closed. Preferably, the package is diffusion-tight. The package can, for example, be a cartridge. It is also possible for the package to be contained in a cartridge. The cartridge can be part of an application device for bone cement paste. The application device can preferably contain a mixing device. The mixing device can be suitable for mixing individual components of a kit for producing bone cement to generate a bone cement paste.

A time of action of compound (a) on the polymerizable monomer of at least 20 minutes, and more preferably of at least 30 minutes, has proven to be advantageous for the method according to the invention for sterilization of a polymerizable monomer.

Moreover, it is preferable for the temperature for sterilization of a polymerizable monomer at which compound (a) acts on the polymerizable monomer in the method according to the invention to be higher than or equal to the melting temperature of the polymerizable monomer.

It is a feature of compound (b) that compound (b) can react with compound (a). Different products are obtained upon reacting compound (a) and compound (b) depending on the structures of compounds (a) and (b). Surprisingly, the reaction of compound (a) and compound (b) proceeds at a comparatively slow reaction rate in mixtures containing a polymerizable monomer. Therefore, compound (a) first develops its sterilizing effect in mixtures containing compound (b) before reacting with compound (b). Moreover, the duration of the sterilizing effect of compound (a) can be limited by reacting compound (a) and compound (b).

An essential advantage of the method according to the invention for sterilization of a polymerizable monomer is that the sterilizing effect is provided after producing mixture (I) in the absence of any additional external factors. Moreover, it is feasible, for example, to fill a suitable package with mixture (I), where the package is preferably diffusion-tight. In this context, compound (a) also contacts the inside of the package such that not only the polymerizable monomer and additional optional components that may be contained in mixture (I) are sterilized, but the inside of the package is sterilized as well.

A mixture (II) can also be obtained by carrying out the method according to the invention for sterilization of a polymerizable monomer. Mixture (II) comprises at least one polymerizable monomer. The polymerizable monomer is preferably a polymerizable monomer according to the preceding description in the context of mixture (I). In addition, mixture (II) contains a compound (c). Compound (c) is obtained by reacting compounds (a) and (b), where compounds (a) and (b) are as described above.

The reaction of compounds (a) and (b) preferably proceeds at room temperature and without any need for further external measures in the process. Different products are obtained upon reacting compounds (a) and (b) depending on the structures of compounds (a) and (b).

If compound (b) in mixture (I) is water and compound (a) is a compound (a1) represented by general formula (I), the method according to the invention results in the lactone ring being opened to form a carboxylic acid. Preferably, the carboxylic acid obtained by this method is represented by general formula (V):

$$HOOC-CR_1R_2-CR_3R_4-OH \quad (V)$$

wherein residues R1, R2, R3 and R4, independent of each other, can have the meaning defined above.

If compound (b) in mixture (I) is an alcohol represented by general formula (IV) and compound (a) is a compound (a1) represented by general formula (I), the method according to the invention results in the lactone ring being opened to form an ester. Preferably, the ester obtained by this method is represented by general formula (VI):

$$R7OOC\text{—}CR1R2\text{-}CR3R4\text{-}OH \qquad (VI)$$

wherein residues R1, R2, R3, R4 and R7, independent of each other, can have the meaning defined above.

If compound (b) in mixture (I) is water and compound (a) is a compound (a2) represented by general formula (II), the method according to the invention results in the lactone ring being opened to form a carboxylic acid. Preferably, the carboxylic acid obtained by this method is represented by general formula (VII):

$$HOOC\text{—}CR1R2\text{-}CR3(OH)\text{—}CH2\text{-}CR3(OH)\text{—}\\CR1R2\text{-}COOH \qquad (VII)$$

wherein residues R1, R2, and R3, independent of each other, can have the meaning defined above.

If compound (b) in mixture (I) is an alcohol and compound (a) is a compound (a2) represented by general formula (II), the method according to the invention results in the lactone ring being opened to form an ester. Preferably, the ester obtained by this method is represented by general formula (VIII):

$$R7OOC\text{—}CR1R2\text{-}CR3(OH)\text{—}CH2\text{-}CR3(OH)\text{—}\\CR1R2\text{-}COOR7 \qquad (VIII)$$

wherein residues R1, R2, R3, and R7, independent of each other, can have the meaning defined above.

If compound (b) in mixture (I) is water and compound (a) is a compound (a3) represented by general formula (III), the method according to the invention results in the formation of carbon dioxide and at least one alcohol. Preferably, the alcohol obtained by this method is represented by general formula (IX):

$$R5\text{-}OH \qquad (IX)$$

or by general formula (X):

$$R6\text{-}OH \qquad (X)$$

wherein residues R5 and R6, independent of each other, can have the meaning defined above.

If compound (b) in mixture (I) is an alcohol represented by general formula (IV) and compound (a) is a compound (a3) represented by general formula (III), the method according to the invention results in the formation of carbon dioxide, an alcohol, and an ester. Preferably, the alcohol obtained by this method can be represented by general formula (IX):

$$R5\text{-}OH \qquad (IX)$$

or by general formula (X):

$$R6\text{-}OH \qquad (X)$$

wherein residues R5 and R6, independent of each other, can have the meaning defined above.

Preferably, the ester obtained can be represented by general formula (XI):

$$R7O\text{—}CO\text{—}OR7 \qquad (XI)$$

wherein residue R7 can have the meaning defined above.

Compound (c) resulting from the reaction of compound (a) and compound (b), is selected from the group consisting of alcohols, carboxylic acids having at least three carbon atoms, and esters.

According to a preferred embodiment, the alcohol is selected from the group consisting of compounds represented by general formula (V), compounds represented by general formula (VI), compounds represented by general formula (VII), compounds represented by general formula (VIII), compounds represented by general formula (IX), and compounds represented by general formula (X), wherein residues R1, R2, R3, R4, R5, R6, and R7 contained therein, independent of each other, can have the meaning described above.

The carboxylic acid is preferably selected from the group consisting of hydroxycarboxylic acids. Preferably, the hydroxycarboxylic acid is a β-hydroxycarboxylic acid. According to a preferred embodiment, the carboxylic acid is selected from the group consisting of compounds represented by general formula (V) and compounds represented by general formula (VII), wherein residues R1, R2, R3, and R4 contained therein, independent of each other, can have the meaning described above.

The ester is preferably selected from the group consisting of hydroxyesters and diesters. Preferably, the hydroxyester is a β-hydroxyester. Preferably, the diester can be a carbonic acid diester. According to a preferred embodiment, the ester is selected from the group consisting of compounds represented by general formula (VI), compounds represented by general formula (VIII), and compounds represented by general formula (XI), wherein residues R1, R2, R3, R4 and R7 contained therein, independent of each other, can have the meaning described above.

According to a preferred embodiment, compound (c) is selected from the group consisting of compounds represented by general formula (V), compounds represented by general formula (VI), compounds represented by general formula (VII), compounds represented by general formula (VIII), compounds represented by general formula (IX), compounds represented by general formula (X), and compounds represented by general formula (XI), wherein residues R1, R2, R3, R4, R5, R6, and R7 contained therein, independent of each other, can have the meaning described above.

According to a particularly preferred embodiment, compound (c) is selected from the group consisting of 3-hydroxypropionic acid and 3-hydroxypropionic acid esters.

Preferably, the fraction of compound (c) in mixture (II) is at least 0.0001% by weight, more preferably at least 0.001% by weight, even more preferably at least 0.01% by weight, and particularly preferably at least 0.1% by weight, relative to the total weight of mixture (II). Preferably, the fraction of compound (c) is no more than 5.0% by weight, more preferably no more than 2.0% by weight, even more preferably no more than 1.0% by weight, and particularly preferably no more than 0.5% by weight, relative to the overall weight of mixture (II). The fraction of compound (c) in mixture (II) is preferably in the range of 0.0001-5.0% by weight, more preferably in the range of 0.001-2.0% by weight, even more preferably in the range of 0.01-1.0% by weight, and particularly preferably in the range of 0.1-0.5% by weight, relative to the total weight of mixture (II).

In addition to the polymerizable monomer and compound (c), mixture (II) can optionally contain additional components (d). These additional components (d) preferably are the additional components (d) according to the preceding description in the context of mixture (I).

According to a preferred embodiment, mixture (II) containing at least the polymerizable monomer and compound (c), is present in a package. Preferably, the package is closed. Preferably, the package is diffusion-tight. The package can, for example, be a cartridge. It is also possible for the package to be contained in a cartridge. The cartridge can be part of an application device for bone cement paste. The application device can preferably contain a mixing device. The mixing device can be suitable for mixing individual components of a kit for producing bone cement to generate a bone cement paste.

The invention also provides a kit for producing bone cement, the kit comprising at least a paste A and a paste B. At least one of pastes A and B contains one of the mixtures (II) described above. Preferably, paste A and paste B each contain one of the mixtures (II) described above, wherein paste A differs from paste B in at least one of its components.

Pastes A and B can contain at least one additional component aside from the polymerizable monomer and compound (c). The additional component can be selected from the group of additional components (d) described above.

According to a preferred embodiment, paste A comprises a polymerizable monomer, in particular a monomer for radical polymerization, a compound (c), and a polymer (d1) soluble in the polymerizable monomer, and paste B comprises at least one polymerizable monomer, a compound (c), and a polymer (d1) soluble in the polymerizable monomer. Preferably, at least one of the pastes A and B also contains a polymer (d2) insoluble in the polymerizable monomer. A polymer (d2) insoluble in the polymerizable monomer can also be contained in paste A and paste B. Moreover, at least one of the pastes A and B contains at least one radical polymerization initiator (d3). Preferably, the radical polymerization initiator (d3) is contained in the same paste that contains the polymer (d2) insoluble in the polymerizable monomer. Furthermore, it is preferable that at least one of the pastes A and B comprises a polymerization activator (d4). Moreover, it is preferred that at least one of the pastes A and B contains a pharmaceutical agent (d7).

According to a particularly preferred embodiment, paste A and paste B are present in the kit for producing bone cement in a first package and a second package, respectively. Preferably, the packages are spatially separated from each other. The packages are also preferably closed. Moreover, the packages are preferably diffusion-tight. The packages can, for example, be cartridges. It is also possible for the packages to be contained in cartridges. The cartridges can be part of an application device for bone cement paste. The application device can preferably contain a mixing device. The mixing device can be suitable for mixing individual components of a kit for producing bone cement to generate a bone cement paste.

The invention also relates to a bone cement paste. In this context, bone cement shall be understood to mean a paste that can be applied to a patient and can self-harden. The bone cement paste contains a mixture (II) according to the preceding definition.

According to a preferred embodiment, the bone cement paste contains at least one additional component. The additional component can be selected from the group of additional components (d) described above.

According to a particularly preferred embodiment, the bone cement paste comprises, according to the invention, aside from the polymerizable monomer and compound (c), at least one polymer (d1) soluble in the polymerizable monomer, one polymer (d2) insoluble in the polymerizable monomer, an optional radical polymerization initiator (d3), an optional polymerization activator (d4), and an optional pharmaceutical agent (d7).

EXAMPLES

The invention is illustrated in more detail by the following examples. It is to be understood that the examples do not limit the scope of the invention. Examples 1-7 and Reference Examples 1-2

Example 1

A total of 20 g methylmethacrylate (Sigma-Aldrich, stabilized with hydroquinone) each were weighed out into five 50 ml screw cap vessels. After adding 14 µl distilled water, 10 µl of a 40% ethanolic *Bacillus subtilis* ATCC 9357 spore suspension were added to each of the screw cap vessels. Then 17 µl (20 mg) β-propiolactone were added. The screw cap vessels were closed, shaken thoroughly for a short period of time, and stored for seven days at 23° C.

Example 2

A total of 20 g methylmethacrylate (Sigma-Aldrich, stabilized with hydroquinone) each were weighed out into five 50 ml screw cap vessels. After adding 35 µl distilled water, 10 µl of a 40% ethanolic *Bacillus subtilis* ATCC 9357 spore suspension were added to each of the screw cap vessels. Then 34 µl (40 mg) β-propiolactone were added. The screw cap vessels were closed, shaken thoroughly for a short period of time, and stored for seven days at 23° C.

Example 3

A total of 20 g methylmethacrylate (Sigma-Aldrich, stabilized with hydroquinone) each were weighed out into five 50 ml screw cap vessels. After adding 20 µl methanol, 10 µl of a 40% ethanolic *Bacillus subtilis* ATCC 9357 spore suspension were added to each of the screw cap vessels. Then 17 µl (20 mg) β-propiolactone were added. The screw cap vessels were closed, shaken thoroughly for a short period of time, and stored for seven days at 23° C.

Example 4

A total of 20 g methylmethacrylate (Sigma-Aldrich, stabilized with hydroquinone) each were weighed out into five 50 ml screw cap vessels. After adding 34 µl distilled water, 10 µl of a 40% ethanolic *Bacillus subtilis* ATCC 9357 spore suspension were added to each of the screw cap vessels. Then 34 µl (40 mg) dimethyldicarbonate were added. The screw cap vessels were closed, shaken thoroughly for a short period of time, and stored for seven days at 23° C.

Reference Example 1

A total of 20 g methylmethacrylate (Sigma-Aldrich, stabilized with hydroquinone) each were weighed out into five 50 ml screw cap vessels. Then 10 µl of a 60% ethanolic *Bacillus subtilis* ATCC 9357 spore suspension were added to each of the screw cap vessels. The screw cap vessels were closed, shaken thoroughly for a short period of time, and stored for seven days at 23° C.

Example 5

A total of 8.0 g methylmethacrylate (Sigma-Aldrich, stabilized with hydroquinone) each were weighed out into five 50 ml screw cap vessels. After adding 14 µl distilled water, 10 µl of a 60% ethanolic *Bacillus subtilis* ATCC 9357 spore suspension, and 17 µl (20 mg) β-propiolactone were added to each of the screw cap vessels. The preparations were then shaken briefly to homogenize the mixture. Then a mixture of 1.0 g zirconium dioxide, 5.5 g of a linear polymethylmethacrylate-co-methacrylate, and 5.5 g of a cross-linked polymethylmethacrylate was added to each of the screw cap vessels. A paste was thus formed. The preparations were then shaken briefly. The preparations were then stored at 23° C. for seven days.

Example 6

A total of 8.0 g methylmethacrylate (Sigma-Aldrich, stabilized with hydroquinone) each were weighed out into five 50 ml screw cap vessels. After adding 35 µl distilled water, 10 µl of a 60% ethanolic *Bacillus subtilis* ATCC 9357 spore suspension, and 35 µl (40 mg) β-propiolactone were added to each of the screw cap vessels. The preparations were then shaken briefly to homogenize the mixture. Then a mixture of 1.0 g zirconium dioxide, 5.5 g of a linear polymethylmethacrylate-co-methacrylate, and 5.5 g of a cross-linked polymethylmethacrylate was added to each of the screw cap vessels. A paste was thus formed. The preparations were then shaken briefly. The preparations were then stored at 23° C. for seven days.

Example 7

A total of 8.0 g methylmethacrylate (Sigma-Aldrich, stabilized with hydroquinone) each were weighed out into five 50 ml screw cap vessels. After adding 20 µl methanol, 10 µl of a 60% ethanolic *Bacillus subtilis* ATCC 9357 spore suspension, and 35 µl (40 mg) β-propiolactone were added to each of the screw cap vessels. The preparations were then shaken briefly to homogenize the mixture. Then a mixture of 1.0 g zirconium dioxide, 5.5 g of a linear polymethylmethacrylate-co-methacrylate, and 5.5 g of a cross-linked polymethylmethacrylate was added to said preparation in each of the screw cap vessels. A paste was thus formed. The preparations were then shaken briefly. The preparations were then stored at 23° C. for seven days.

Reference Example 2

A total of 8.0 g methylmethacrylate (Sigma-Aldrich, stabilized with hydroquinone) each were weighed out into five 50 ml screw cap vessels. Then 10 µl of a 60% ethanolic *Bacillus subtilis* ATCC 9357 spore suspension were added to each of the plastic bottles. The preparations were then shaken briefly to homogenize the mixture. Then a mixture of 1.0 g zirconium dioxide, 5.5 g of a linear polymethylmethacrylate-co-methacrylate, and 5.5 g of a cross-linked polymethylmethacrylate was added to said preparation in each of the screw cap vessels. The preparations were then shaken briefly. A paste was thus formed. The preparations were then stored at 23° C. for seven days.

Analysis of Examples 1-7 and Reference Examples 1-2

For analysis, the mixtures obtained in the examples and reference examples were tested for sterility. For this purpose, two samples were taken from each screw cap vessel after seven days of incubation. The samples were then incubated for 14 days and then tested for sterility in accordance with ISO11737 part 2. The results are shown in Table 1:

TABLE 1

Test for sterility of the mixtures of examples 1-7 and reference examples 1 and 2 in accordance with ISO 11737 part 2.

| Example | Number of sterile samples | Number of non-sterile samples |
| --- | --- | --- |
| 1 | 8 | 2 |
| 2 | 10 | 0 |
| 3 | 10 | 0 |
| 4 | 10 | 0 |
| Reference example 1 | 2 | 8 |
| 5 | 10 | 0 |
| 6 | 10 | 0 |
| 7 | 10 | 0 |
| Reference example 2 | 2 | 8 |

Example 8

In the following, a paste A and a paste B were prepared by mixing the educts in separate screw cap vessels.

| Paste A | |
| --- | --- |
| Educt | Weight |
| 1-Cyclohexyl-5-ethyl-barbituric acid | 2.0 g |
| Methacrylamide | 0.4 g |
| Methylmethacrylate | 18.9 g |
| Linear methylmethacrylate-soluble polymethylmethacrylate-co-methylacrylate (molar mass <500,000 g/mol) | 6.2 g |
| Cross-linked polymethylmethacrylate (sieve fraction <100 µm) | 15.5 g |
| 2,4-Di-t-butyl-4-methyl-phenol | 20 mg |
| β-Propiolactone | 86 mg |
| Water | 86 mg |

| Paste B | |
| --- | --- |
| Educt | Weight |
| Lithium chloride | 40 mg |
| 2,4-Di-t-butyl-4-methyl-phenol | 35 mg |
| Methylmethacrylate | 18.9 g |
| Linear methylmethacrylate-soluble polymethylmethacrylate-co-methylacrylate (molar mass <500,000 g/mol) | 16.9 g |
| Green lacquer | 50 mg |
| Copper(II) hydroxide | 2 mg |
| β-Propiolactone | 86 mg |
| Water | 86 mg |

The two pastes were then stored at room temperature for seven days. Then 3.5 g of paste A and 3.5 g of paste B were taken and kneaded together thoroughly. A green, non-tacky cement dough was thus produced. The dough was kneaded further by hand. After approximately 2 minutes and 40 seconds, the initiation of polymerization was notable by the release of heat. The end of processability was reached after 4 minutes and 40 seconds. The cement dough was fully cured after approximately 6 minutes.

Example 9

In the following, a paste A and a paste B were prepared by mixing the educts in separate screw cap vessels.

Paste A

| Educt | Weight |
| --- | --- |
| 1-Cyclohexyl-5-ethyl-barbituric acid | 2.0 g |
| Methacrylamide | 0.4 g |
| Methylmethacrylate | 18.9 g |
| Linear methylmethacrylate-soluble polymethylmethacrylate-co-methylacrylate (molar mass <500,000 g/mol) | 6.2 g |
| Cross-linked polymethylmethacrylate (sieve fraction <100 μm) | 15.5 g |
| 2,4-Di-t-butyl-4-methyl-phenol | 20 mg |
| β-Propiolactone | 86 mg |
| Water | 86 mg |

Paste B

| Educt | Weight |
| --- | --- |
| Aliquat 336 (trioctylmethylammoniumchloride) | 60 mg |
| 2,4-Di-t-butyl-4-methyl-phenol | 35 mg |
| Methylmethacrylate | 18.9 g |
| Linear methylmethacrylate-soluble polymethylmethacrylate-co-methylacrylate (molar mass <500,000 g/mol) | 16.9 g |
| Green lacquer | 50 mg |
| Copper(II) hydroxide | 2 mg |
| β-Propiolactone | 86 mg |
| Water | 86 mg |

The two pastes were stored at room temperature for a period of seven days. Then 3.5 g of paste A and 3.5 g of paste B were taken and kneaded together thoroughly. A green, non-tacky cement dough was thus produced. The dough was kneaded further by hand. A release of heat was noted after approximately 3 minutes. The end of processability was reached after 4 minutes 40 seconds. The cement dough was fully cured after approximately 6 minutes and 20 seconds.

Example 10

In the following, a paste A and a paste B were prepared by mixing the educts in separate screw cap vessels.

Paste A

| Educt | Weight |
| --- | --- |
| 1-Cyclohexyl-5-ethyl-barbituric acid | 2.0 g |
| Methacrylamide | 0.4 g |
| Methylmethacrylate | 18.9 g |
| Linear methylmethacrylate-soluble polymethylmethacrylate-co-methylacrylate (molar mass <500,000 g/mol) | 11.5 g |
| Cross-linked polymethylmethacrylate (sieve fraction <100 μm) | 7.7 g |
| 2,4-Di-t-butyl-4-methyl-phenol | 20 mg |
| β-Propiolactone | 86 mg |
| Water | 86 mg |

Paste B

| Educt | Weight |
| --- | --- |
| Aliquat 336 (trioctylmethylammoniumchloride) | 60 mg |
| 2,4-Di-t-butyl-4-methyl-phenol | 35 mg |
| Methylmethacrylate | 18.9 g |
| Linear methylmethacrylate-soluble polymethylmethacrylate-co-methylacrylate (molar mass <500,000 g/mol) | 11.5 g |
| Cross-linked polymethylmethacrylate (sieve fraction <100 μm) | 7.7 g |
| Green lacquer | 50 mg |
| Copper(II) hydroxide | 2 mg |
| β-Propiolactone | 86 mg |
| Water | 86 mg |

The two pastes were then stored at room temperature for seven days. Then 3.5 g of paste A and 3.5 g of paste B were taken and kneaded together thoroughly. A green, non-tacky cement dough was thus produced. The dough was kneaded further by hand. The end of processability was reached after 5 minutes. The cement dough was fully cured after approximately 6 minutes.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for sterilization of a polymerizable monomer, the method comprising mixing at least the polymerizable monomer, an acylating agent, and a compound (b), wherein:
    (i) the acylating agent is selected from one of compounds (a1), (a2), and (a3), wherein compound (a1) is a compound represented by formula (I):

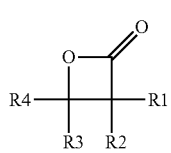

wherein R1, R2, R3, and R4 independently represent a hydrogen, a substituted alkyl residue, a non-substituted alkyl residue, a halogen, a nitro group, or a cyano group;
wherein compound (a2) is selected from the group consisting of dimers of compounds (a1); and
wherein compound (a3) is selected from the group consisting of dialkyldicarbonates; and
    (ii) the compound (b) is selected from the group consisting of water and alcohols, thereby producing a paste, such that the polymerizable monomer is sterilized in the paste, and wherein a fraction of compound (b) in the paste is no more than 2% by weight relative to a total weight of the paste.

2. The method according to claim 1, wherein a fraction of compound (b) in the paste is no more than 0.4% by weight, relative to the total weight of the paste.

3. The method according to claim 1, wherein the polymerizable monomer is a monomer for radical polymerization.

4. The method according to claim 1, wherein the acylating agent is β-propiolactone.

5. The method according to claim 1, wherein the polymerizable monomer and compound (b) are the same compound.

6. The method according to claim 1, wherein a ratio of the quantity $n_b$ of compound (b) in the paste to the quantity $n_a$ of the acylating agent in the paste is represented by the equation $n_b/n_a > 0.5$.

* * * * *